United States Patent [19]

Miller et al.

[11] 4,215,939
[45] Aug. 5, 1980

[54] GLUE DROP DETECTOR

[75] Inventors: John W. V. Miller, Toledo; James A. Ringlien, Maumee, both of Ohio

[73] Assignee: Owens-Illinois, Inc., Toledo, Ohio

[21] Appl. No.: 863,201

[22] Filed: Dec. 22, 1977

[51] Int. Cl.² .................. G01B 11/30; G01N 21/48; G01N 21/32
[52] U.S. Cl. .................. 356/371; 356/445; 356/430; 250/572; 356/237
[58] Field of Search ............... 356/209, 237, 129, 445, 356/446, 430, 371; 250/572

[56] References Cited

U.S. PATENT DOCUMENTS

| 3,245,306 | 4/1966 | Potter et al. | 356/209 |
| 3,484,150 | 12/1969 | Tadka et al. | 356/237 X |
| 3,767,306 | 10/1973 | Mast et al. | 356/129 X |

FOREIGN PATENT DOCUMENTS 2354141 10/1972 Fed. Rep. of Germany .......... 356/371

OTHER PUBLICATIONS

Dalton, Bright Field Reflective Schlieren System, IBM Technical Disclosure Bulletin, Jun. 1971.

Primary Examiner—Vincent P. McGraw
Assistant Examiner—Rodney B. Bovernick
Attorney, Agent, or Firm—John R. Nelson; David H. Wilson; Myron E. Click

[57] ABSTRACT

This invention relates to a method and apparatus for determining whether a glue drop is present on the reflective inner surface of a closure. Collimated light is projected onto the reflective inner surface of the closure, and a measurement is taken of the amount of light which remains collimated after reflection from the closure. The measurement of the amount of light reflected in this way is used to determine whether a glue drop is present.

11 Claims, 3 Drawing Figures

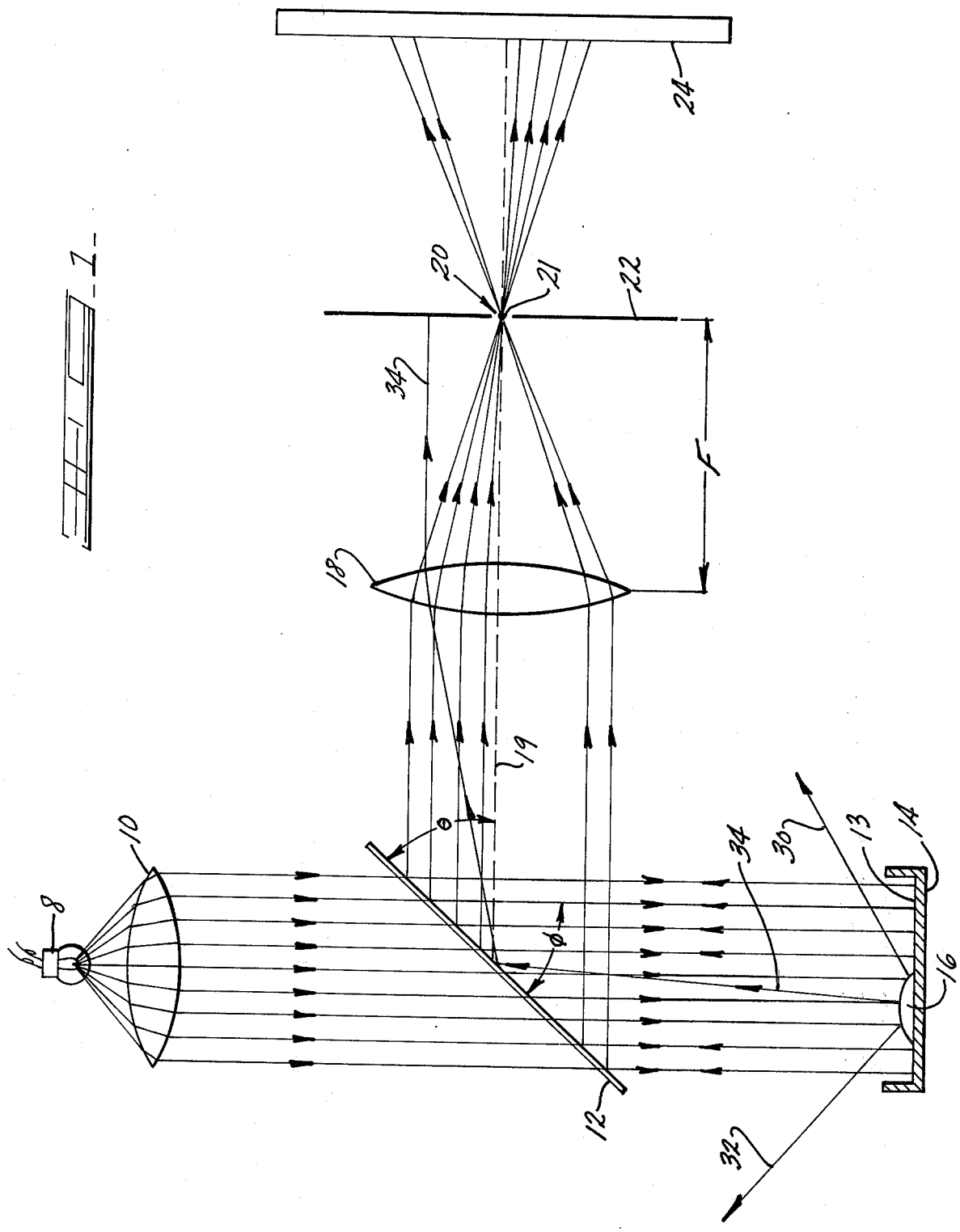

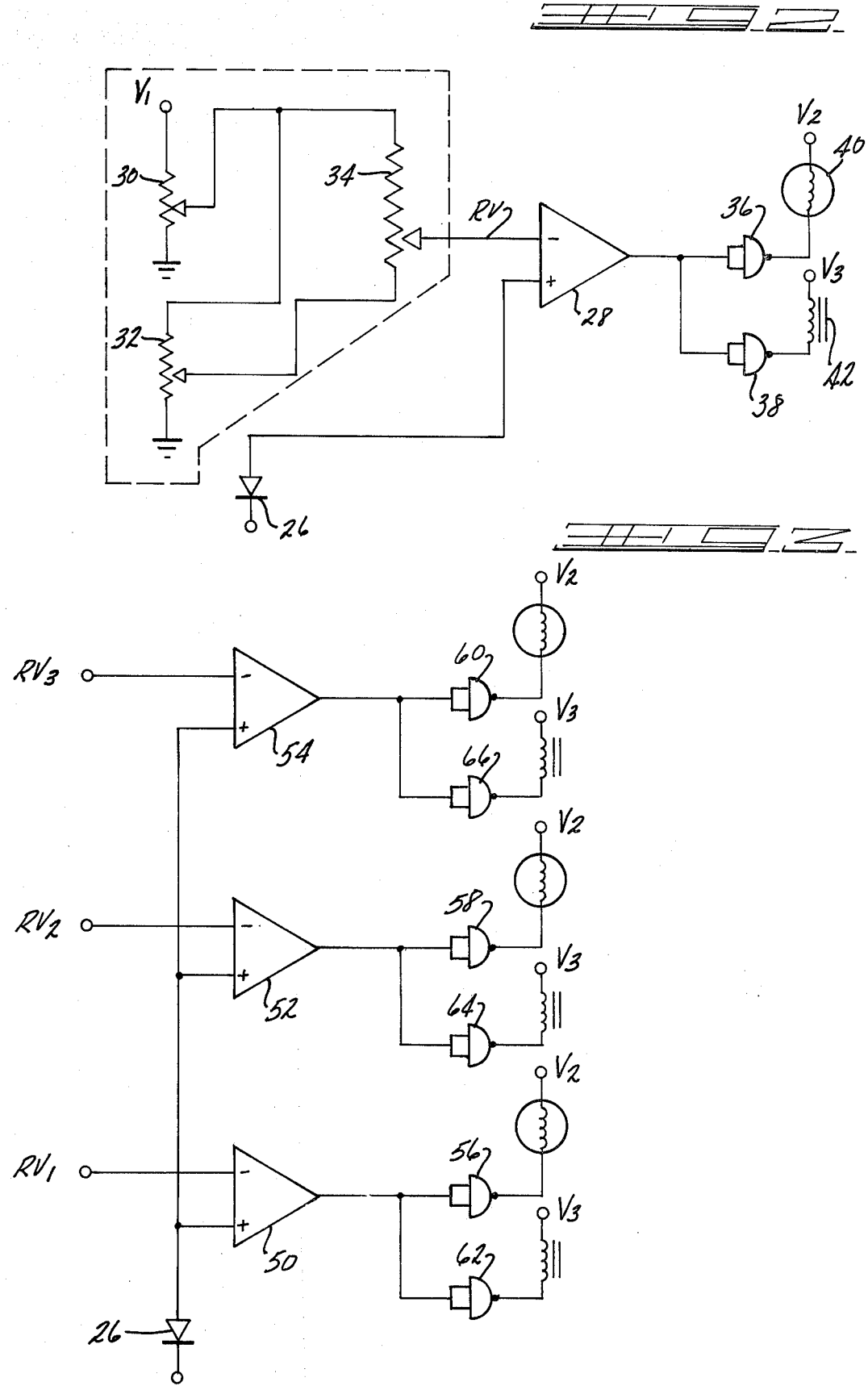

GLUE DROP DETECTOR

BACKGROUND

Closures often contain an inner liner which is used to form a more complete seal between the closure and a container. The liner may be secured to the closure by the use of glue. A drop of glue is deposited on the inner surface of a closure and the liner is affixed later. In order to make sure that the glue drop is being deposited on the closure properly, it is necessary to check to see if a glue drop is present before attaching a liner. Previously, this has been accomplished by either visual inspection or by the use of an infrared detector, which can be used only when the glue drop is relatively hot when it is deposited on the closure surface.

Principal advantages of the present invention are that visual inspection of the closure is not needed and that there is no need for a temperature gradient between the glue drop and closure surface.

SUMMARY OF THE INVENTION

Collimated light is projected onto a closure which has a reflective flat inner surface. The amount of light which remains collimated after reflection from the closure depends upon whether a glue drop is present, since light striking a glue drop will diverge upon reflection. A measurement is taken of the amount of light which remains collimated after reflection from the closure. If this amount exceeds a predetermined level, a glue drop is assumed not to be present.

BRIEF DESCRIPTION OF THE DRAWINGS

FIG. 1 shows an optical apparatus used for detecting light which remains collimated after reflection from a closure.

FIG. 2 shows a schematic diagram of a circuit used for determining whether a glue drop is present on a closure.

FIG. 3 shows an addition to the circuit of FIG. 2 to allow for a reading of the relative size of glue drops.

DETAILED DESCRIPTION OF THE DRAWINGS

Referring to FIG. 1, light from a light source 8, located at the focal point of a converging lens 10, is passed through the lens 10 (which causes the light emanating from the lens 10 to be collimated), through a beam splitter 12 and projected onto the reflective flat inside surface 13 of a closure 14. The light is reflected from the closure 14 back to the beam splitter 12, from which it is reflected to a second converging lens 18, having an optic axis 19 and a focal point 21. The lens 18 is positioned so that the angle of intersection $\theta$ of its axis 19 with the beam splitter 12 is equal to the angle of incidence $\phi$ of light reflected from the flat inside surface 13 of the closure 14. In this way, light travelling to the lens 18 from the beam splitter 12 after having been reflected from the flat inside surface 13 of closure 14 will be parallel to optic axis 19. This light will then pass through the lens 18, through focal point 21 and strike a detector plane 24.

Referring further to FIG. 1, a glue drop 16, located on the inside surface of closure 14 will reflect light from the light source at different angles than the flat inside surface 13 of closure 14, due to its convex shape. Much of that light will be reflected from the glue drop 16 at an angle large enough such that it will not strike the beam splitter 12 at all, as illustrated by light rays 30 and 32. Rays which are reflected from the glue drop 16 at smaller angles, such as ray 34, will strike the beam splitter 12 and be reflected through the lens 18. However, since it is not parallel to light reflected from the flat inside surface 13 of closure 14, this light will not enter the lens 18 parallel to its optic axis 19, and will therefore not pass through the focal point 21. A screen 22, located at a distance from the lens 18 equal to its focal length (i.e. in the focal plane) and including an aperture 20 at focal point 21, prevents any light passing through the lens 18 which was not parallel to the optic axis 19 from striking the detector plane 24. Light which is parallel to the optic axis 19 will pass through the aperture 20 and strike the detector plane 24. From the foregoing it is clear that a bright image of the flat inside surface of the cap 14 will be formed on the detector plane 24 with a dark spot in the image corresponding to the presence of a glue drop 14. The dark spot will have a highlight near its center corresponding to reflection from the top of the glue drop 16, since this portion of the glue drop 16 is parallel to the inside surface 13 of the closure 14 and light reflected from it will then enter the lens 18 parallel to its optic axis 19. In addition, the image formed on the plane 24 will be in best focus when the inside surface 13 of the closure 14 and the detector plane 24 are at conjugate distances (with respect to the light path) from the lens 18.

Referring now to FIG. 2, a photodetector 26 is positioned at the detector plane 24 to receive light reflected from a closure 14. The signal from the photodetector 26 is then fed to the positive input of a comparator 28, where it is compared to a reference voltage RV. If the signal from the photodetector is greater than the reference voltage RV the output of the comparator will go to the high state. Since a closure 14 without a glue drop 16 will reflect more light than a closure 14 with a glue drop 16, the signal to the comparator 28 from the photodetector 26 will be greater when no glue drop 16 is present. The reference voltage RV is set to a value which is between the voltage of the photodetector 26 corresponding to the presence of a glue drop 16 in a closure 14 and the voltage of the photodetector 26 corresponding to the absence of a glue drop 16. It can thus be seen that when a glue drop 16 is not present, the voltage from the photodetector 26 will be greater than the reference voltage, causing the comparator 28 to go to the high state.

In the preferred embodiment of the invention, the reference voltage RV is obtained by placing a bias potentiometer 34 between voltage sources of values equal to the no drop voltage and the drop voltage. In this way, the threshold of the comparator may be varied from a value just above the drop voltage to just below the no drop voltage. In order to obtain a no drop voltage, a variable potentiometer 30, fed by supply voltage $V_1$, is set to obtain a voltage corresponding to the average voltage of several readings taken from closures 14 without glue drops 16. The drop voltage may be similarly obtained from another supply voltage feeding a variable potentiometer 32. In the preferred embodiment of the invention, the no drop voltage is used as the supply voltage to obtain the drop voltage. In this way the drop voltage proportionately tracks the no drop voltage, so that changes in reflective qualities of closures 14 (and thus average voltage levels of the photodetector 26), may be conveniently compensated for by varying only the one potentiometer 30. It is to be appreciated that the drop and no drop voltages could be controlled entirely separately from one another, and that the purpose in obtaining these voltages is simply to obtain the reference voltage RV which is between the voltages corresponding to the presence and absence of a glue drop 16 in a closure 14.

The signal from the comparator 28 is utilized to control a no drop indicator 40 and a relay 42. When a glue drop 16 is present, the output of the comparator 28 is low and the outputs of power NAND gates 36 and 38 are high. In this case there is no voltage drop across indicator 40 or relay 42. When the comparator signal goes high, the outputs of NAND gates 36 and 38 are pulled to ground. This causes a potential drop across indicator 40 and relay 42, fed by voltage supplies $V_2$ and $V_3$, causing them both to switch on. The indicator 40 signal may be utilized for monitoring, while the relay 42 may be used to switch an automatic ejector or the like.

Referring now to FIG. 3, a plurality of reference voltages, e.g. $RV_1$, $RV_2$, and $RV_3$ may be utilized to determine the relative size of a glue drop 16 on a closure 14. The $RV_1$ reference voltage is set to a level corresponding to the smallest useable glue drop 16 while the other reference voltages $RV_2$ and $RV_3$ are set at correspondingly higher levels. As each reference level is exceeded, comparators 50, 52, and 54 can be used to switch indicators and/or relays 56, 58 and 60 and 62, 64, and 66 (again fed by supply voltages $V_2$ and $V_3$) in the same manner as described in connection with FIG. 2. In this way the presence detector is modified to include indication of the relative size of a glue drop 16.

What is claimed is:

1. A method for determining whether a glue drop is present on the inside of a closure comprising the steps of:
   (a) projecting collimated light through a beam splitter and onto the generally flat reflective inside surface of a closure, said beam splitter being positioned so that it receives reflections from said closure inside surface; and
   (b) measuring the amount of light which remains collimated after reflection from the inside closure surface, with a relatively greater amount of light remaining collimated after reflection when a glue drop is not present.

2. The method of claim 1 wherein step b includes the steps of:
   (a) passing light which has been reflected from said beam splitter through a converging lens, said lens being positioned so that light which remains collimated after reflection from said closure inner surface enters the lens parallel to its optic axis, thus passing through the focal point of said lens;
   (b) blocking out all light which does not pass through the focal point of said lens; and
   (c) measuring the amount of light which does pass through the focal point of said lens.

3. The method of claim 1 wherein step b includes measuring the amount of light reflected from said closure inner surface with a photoelectric detector.

4. The method of claim 3 including the steps of:
   (a) comparing the output of said photoelectric detector to a reference signal, the value of which is less than the average output of the photoelectric detector when a glue drop is not present; and
   (b) generating a signal, said signal indicating the absence of a glue drop, whenever the output of the photoelectric detector is less than the value of the reference signal.

5. Apparatus for determining whether a glue drop is present on the inside of a closure having a generally flat reflective inner surface comprising:
   (a) means for projecting collimated light onto the inside surface of said closure;
   (b) a beam splitter located such that said collimated light passes through it before striking said closure inner surface and so that light which remains collimated after relfection from said closure inner surface strikes the beam splitter and is reflected off it; and
   (c) means for measuring the amount of light which remains collimated after reflection from said closure inner surface, with a relatively greater amount of light remaining collimated after reflection from a closure without a glue drop.

6. The apparatus of claim 5 further comprising:
   means for comparing the amount of light which remains collimated after reflection from said closure inner surface and a reference level, the value of which is less than the average amount of light which remains collimated after reflection from closures without a glue drop and greater than the average amount of light which remains collimated after reflection from closures with a glue drop; and
   means for generating an indicator and control signal whenever the amount of light which remains collimated after reflection exceeds said reference level.

7. The apparatus of claim 6 wherein said comparing means includes:
   a comparator, the output of which is used as a trigger to indicate the presence of glue drop and to activate a control signal for reflecting closures without a glue drop;
   a reference voltage, the value of which corresponds to said reference level, feeding one input of said comparator; and
   a photoelectric detector, said detector receiving light which remains collimated after reflection from said closure inner surface, feeding the other input of said comparator.

8. The apparatus of claim 5 wherein said means for projecting collimated light includes a converging lens and a light source located at the focal point of said lens.

9. The apparatus of claim 5 further comprising a converging lens, said lens being located so that it receives reflections from said beam splitter and oriented so that light which remains collimated after reflection from said closure inner surface enters the lens parallel to its optic axis.

10. The apparatus of claim 9 further comprising a screen located in the focal plane of said lens, said screen having an aperture at the focal point of said lens, thus allowing only light which enters said lens parallel to its optic axis to pass through said screen.

11. The apparatus of claim 10 further comprising a photoelectric detector located behind said screen so that it receives all light which passes through said aperture.

* * * * *